(12) United States Patent
Donaghy et al.

(10) Patent No.: US 11,865,063 B2
(45) Date of Patent: Jan. 9, 2024

(54) DEFIBRILLATOR ASSESSING CHEST RECOIL IN CARDIO PULMONARY RESUSCITATION

(71) Applicant: HeartSine Technologies Limited, Belfast (GB)

(72) Inventors: Dymphna Mary Donaghy, County Donegal (IE); Johnny Houston Anderson, Holywoor (GB); Olibhear Oisin Gerard McAlister, Belfast (GB); Adam Patrick Harvey, Hillsborough (GB)

(73) Assignee: HeartSine Technologies Limited, Belfast (GB)

( * ) Notice: Subject to any disclaimer, the term of this patent is extended or adjusted under 35 U.S.C. 154(b) by 487 days.

(21) Appl. No.: 17/181,129

(22) Filed: Feb. 22, 2021

(65) Prior Publication Data
US 2021/0308002 A1 Oct. 7, 2021

(30) Foreign Application Priority Data
Apr. 3, 2020 (GB) ..................... 2004936

(51) Int. Cl.
| | |
|---|---|
| *A61H 31/00* | (2006.01) |
| *G16H 20/30* | (2018.01) |
| *G16H 40/67* | (2018.01) |
| *G16H 15/00* | (2018.01) |

(Continued)

(52) U.S. Cl.
CPC ......... *A61H 31/005* (2013.01); *A61N 1/3987* (2013.01); *G16H 15/00* (2018.01); *G16H 20/30* (2018.01); *G16H 40/67* (2018.01); *G16H 50/70* (2018.01); *A61H 2201/10* (2013.01); *A61H 2201/5007* (2013.01); *A61H 2201/5043* (2013.01); *A61H 2201/5048* (2013.01); *A61H 2230/65* (2013.01); *A61N 1/39044* (2017.08)

(58) Field of Classification Search
CPC .................. A61H 31/00; A61H 31/005; A61H 2201/5043; A61H 2230/65; A61H 2031/001–003; A61H 31/004–008; G16H 16/00; A61N 1/3987; A61N 1/39; A61N 1/39044; A61N 1/3943; A61B 5/1135; A61B 5/085; A61B 5/0809
See application file for complete search history.

(56) References Cited

U.S. PATENT DOCUMENTS

2018/0169426 A1* 6/2018 Montague .............. G16H 40/67

* cited by examiner

*Primary Examiner* — Philip R Wiest
*Assistant Examiner* — Sarah B Lederer

(57) ABSTRACT

According to the disclosure there is provided an apparatus that assesses chest recoil of a subject during cardio pulmonary resuscitation (CPR) carried out by a rescuer on the subject and provides feedback to the rescuer. This apparatus may include a bio-signal measurement system configured to measure bio-signals of the subject. The apparatus may identify when CPR is required and may provide a CPR start signal to indicate when CPR should be started and this apparatus may identify when CPR is to be ceased. A CPR stop signal may be provided to a rescuer to indicate when CPR should be stopped. The apparatus may include electronic circuits capable of measuring impedance signals of the subject, may include sensors that sense bio-signals, and may include defibrillator shock electronics capable of providing a shock to the subject to restart or reset the heart of the subject.

31 Claims, 3 Drawing Sheets

(51) Int. Cl.
*G16H 50/70* (2018.01)
*A61N 1/39* (2006.01)

DEFIBRILLATOR ASSESSING CHEST RECOIL IN CARDIO PULMONARY RESUSCITATION

CROSS-REFERENCE TO RELATED APPLICATIONS

The present disclosure claims priority benefit of patent application 2004936.7 filed with the United Kingdom Patent Office on Apr. 3, 2020, the disclosure of which is incorporated by reference herein in its entirety.

FIELD OF THE DISCLOSURE

This present disclosure is generally directed to resuscitating patients. More specifically, the present disclosure relates to a defibrillator which assesses chest recoil of a subject during performance of cardio pulmonary resuscitation (CPR) by a rescuer.

DESCRIPTION OF THE RELATED ART

Various circumstances may arise when a defibrillator instructs a rescuer to carry out CPR on a subject being treated. CPR involves multiple compressions of the subject's chest by the rescuer to cause the subject's heart to pump blood around their circulatory system, primarily to provide oxygenated blood to the subject's heart and brain. It is important that, following a chest compression, the rescuer allows the subject's chest to completely recoil, i.e. return to its normal position, before the rescuer begins the next chest compression. If this not the case, the subject's heart will not completely refill with blood, the heart will not pump sufficient oxygenated blood and the heart and brain tissue will start to die. For effective CPR, current guidelines recommend complete recoil of a subject's chest. Indeed, the European Resuscitation Council Guidelines for adult basic life support and automated external defibrillation state that a rescuer should: After each compression allow the chest to recoil completely. However, many rescuers do not allow complete recoil of the chest. Defibrillators which assess, and provide feedback concerning, the subject's chest recoil could improve the quality of CPR provided by a rescuer. As such, there is a need to improve defibrillators in ways that helps a rescuer use a defibrillator more effectively.

SUMMARY

Embodiments of the present disclosure are directed to an apparatus, methods, and to non-transitory computer-readable storage media that may monitor cardio pulmonary resuscitation (CPR) of a patient. In one embodiment, an apparatus of the present disclosure includes a sensor that senses an impedance signal associated with chest recoil of a person when CPR is administered to the person. This apparatus also may include a controller that receives the impedance signal sensed by the sensor, identifies an amplitude of the impedance signal associated with the chest recoil of the person, compares the impedance signal amplitude with impedance baseline data, and identifies that a message should be provided to a rescuer based on the comparison of the impedance signal amplitude with the impedance baseline data. This apparatus may also include a user interface that provides the message to the rescuer.

The aforementioned apparatus may also include one or more bio-sensors that sense bio-signals of a person. The controller may analyse data received from the bio-sensors to identify when CPR should be administered to the person or when a shock should be administered to the person. As such, the apparatus may also include a defibrillator capable of delivering a shock to the person defibrillator electronics may provide the shock to the person when required.

The controller may also identify a number of check compressions provided to the person when CPR is being administered and the controller may identify that a stop CPR message should be provided to the rescuer via a user interface based on the identified number of chest compressions.

In another embodiment, a method of the present disclosure may perform the steps of receiving an impedance signal associated with chest recoil of a person, identifying an amplitude of the impedance signal associated with the chest recoil of the person, comparing the impedance signal amplitude with impedance baseline data, identifying that a message should be provided to a rescuer based on the comparison of the impedance signal amplitude with the impedance baseline data, and providing the message to the rescuer. The steps of this method may be performed when CPR is administered to the person.

The aforementioned method may be implemented via a defibrillator or as a non-transitory computer-readable storage medium having embodied thereon a program that includes instructions executable by a processor for implementing a method for evaluating cardio pulmonary resuscitation (CPR). Here again the method may include the steps of receiving an impedance signal associated with chest recoil of a person, identifying an amplitude of the impedance signal associated with the chest recoil of the person, comparing the impedance signal amplitude with impedance baseline data, identifying that a message should be provided to a rescuer based on the comparison of the impedance signal amplitude with the impedance baseline data, and providing the message to the rescuer.

DETAILED DESCRIPTION

Figure 1:
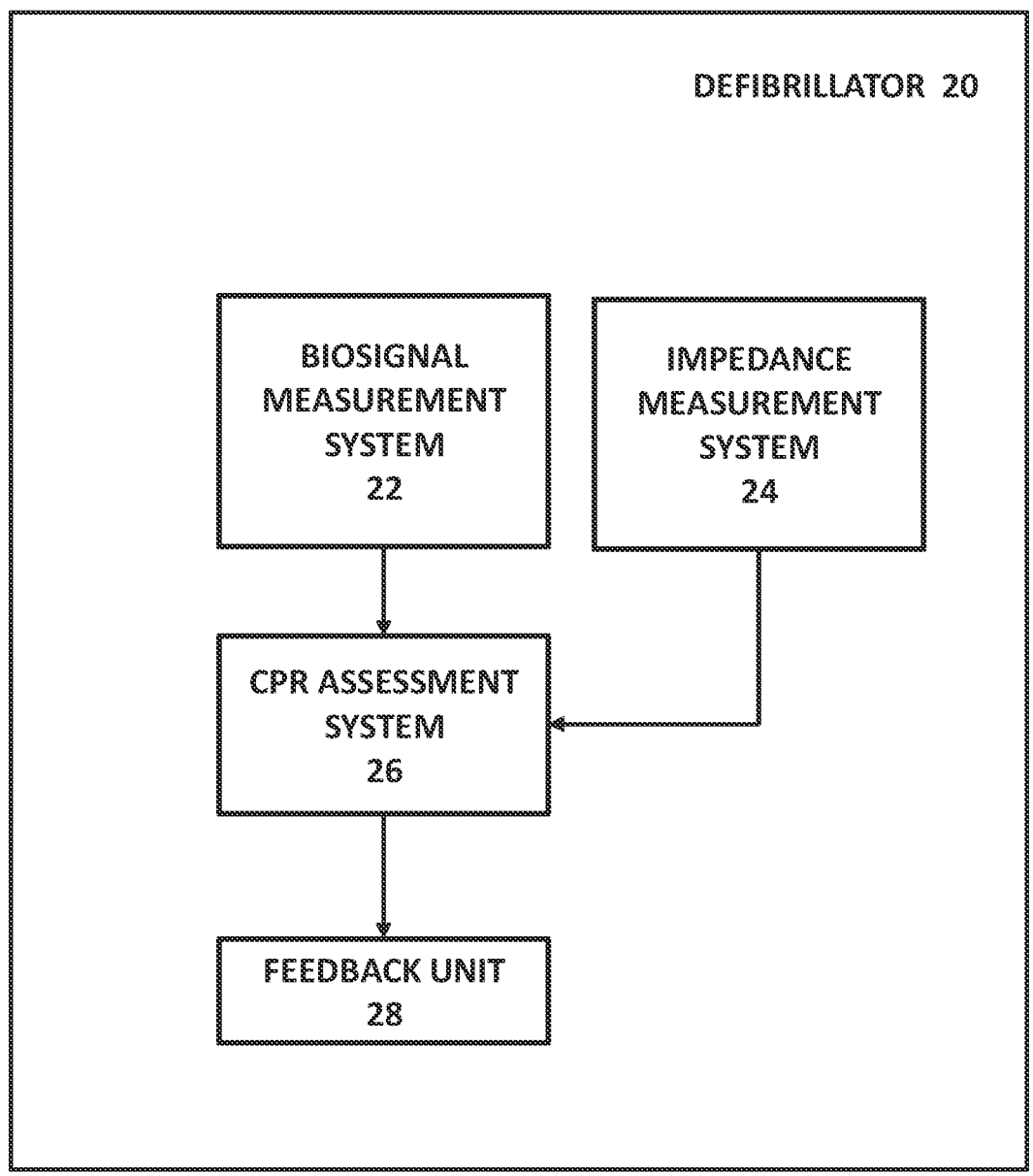
FIG. 1 is a schematic representation of a defibrillator or CPR sensing unit consistent with the present disclosure.

According to the disclosure there is provided a defibrillator which assesses chest recoil of a subject during cardio pulmonary resuscitation (CPR) carried out by a rescuer on the subject and provides feedback to the rescuer, including: a bio-signal measurement system configured to measure bio-signals of the subject, determine when CPR is required and produce a CPR start signal and determine when CPR is to be ceased and produce a CPR stop signal, an impedance measurement system configured to measure impedance signals of the subject, and a CPR assessment system connected to the bio-signal measurement system to receive the CPR start signal and the CPR stop signal. The CPR assessment system is also connected to the impedance measurement system to receive impedance signals and is configured to perform the following exemplary steps:

(i) receive the CPR start signal and produce a first feedback signal, (ii) receive an impedance signal of the subject measured during a plurality of CPR chest compressions by the rescuer,
(iii) use the impedance signal to assess chest recoil of the subject during the plurality of CPR chest compressions,
(iv) compare the chest recoil of the subject with a chest recoil threshold,
(v) when the chest recoil of the subject is greater than the chest recoil threshold, produce a second feedback signal and go to step (vii),
(vi) when the chest recoil of the subject is less than the chest recoil threshold, produce a third feedback signal and go to step (vii),
(vii) when the CPR stop signal is not received, return to step (ii),
(viii) when the CPR stop signal is received, produce a fourth feedback signal, and
a feedback unit connected to the CPR assessment system and configured to receive the feedback signals and issue CPR feedback to the person.

The aim is to achieve as close to complete chest recoil as possible after each CPR chest compression and the defibrillator provides appropriate feedback to the rescuer to try to achieve this.

The CPR assessment system may use the impedance signal to assess chest recoil of the subject during the plurality of CPR chest compressions by measuring a characteristic of the impedance signal after at least some of the plurality of CPR chest compressions. The CPR assessment system may use the impedance signal to assess chest recoil of the subject during the plurality of CPR chest compressions by measuring an amplitude of the impedance signal after at least some of the plurality of CPR chest compressions.

The CPR assessment system may compare the amplitude of the impedance signal after at least some of the plurality of CPR chest compressions with an impedance baseline of the subject. The impedance signal may include a series of peaks and troughs corresponding to the plurality of CPR chest compressions by the rescuer. The CPR assessment system may compare the amplitude of a trough of the impedance signal after at least some of the plurality of CPR chest compressions with the impedance baseline of the subject. The CPR assessment system may compare the amplitude of a peak of the impedance signal after at least some of the plurality of CPR chest compressions with the impedance baseline of the subject.

The CPR assessment system may determine either incomplete chest recoil when the amplitude of the impedance signal after a CPR chest compression is not equal to the impedance baseline or complete chest recoil when the amplitude of the impedance signal after a CPR chest compression is equal to the impedance baseline for at least some of the plurality of CPR chest compressions. The CPR assessment system may determine either incomplete chest recoil when the amplitude of the impedance signal after a CPR chest compression is not within a predetermined tolerance of the impedance baseline or complete chest recoil when the amplitude of the impedance signal after a CPR chest compression is within a predetermined tolerance of the impedance baseline for at least some of the plurality of CPR chest compressions. The predetermined tolerance may be 10% of the amplitude of the impedance signal after a CPR chest compression.

The CPR assessment system may determine a proportion of incomplete chest recoils for the at least some of the plurality of CPR chest compressions. The CPR assessment system may compare the chest recoil of the subject with the chest recoil threshold by comparing the proportion of incomplete chest recoils with the chest recoil threshold. The CPR assessment system may produce the second feedback signal when the proportion of incomplete chest recoils is greater than the chest recoil threshold. The CPR assessment system may produce the third feedback signal when the proportion of incomplete chest recoils is less than the chest recoil threshold. The chest recoil threshold may be a proportion of incomplete chest recoils of 25%.

Feedback signals may be generated based on one or more identifications or determinations made by monitoring devices. Each respective feedback signal of a set of feedback signals may cause messages or indicators to be provided to a rescuer operating a defibrillator. Message may be provided via a speaker (e.g. by a verbal audio message or by a tone of a particular frequency) or may be provided on a display or in some other modality, such as haptic or a combination of different types of modalities. Indicators or messages may include a set of instruction lights or light emitting diodes that illuminate to identify status information associated with particular types of feedback. Indicators or messages provided to a rescuer may include instructions, warnings, or status information that the rescuer may use to improve the efficiency of resuscitating a patient. Such indicators or messages may inform the rescuer to 'start cardio-pulmonary-resuscitation (CPR) and to push hard on the chest of a patient.' These messages may instruct the rescuer that a chest recoil was good—or acceptable, or may inform the rescuer that a chest recoil was incomplete—or unacceptable. Alternatively, or additionally, instructions may inform a rescuer to stop CPR, or may instruct the rescuer to push faster, push slower, or to push softer when applying CPR.

An impedance baseline may be established during at least one period in which no CPR chest compressions are performed by the rescuer. The impedance measurement system may be configured to measure impedance signals during at least one period in which no CPR chest compressions are performed by the rescuer. The CPR assessment system may be configured to receive an impedance signal of the subject measured during the at least one period in which no CPR chest compressions are performed by the rescuer and use the impedance signal to establish the impedance baseline of the subject. The CPR assessment system may use an amplitude of the impedance signal measured during the at least one period to establish the impedance baseline of the subject. The CPR assessment system may be configured to receive an impedance signal of the subject measured during a period before CPR chest compressions by the rescuer and use the impedance signal to establish the impedance baseline. The CPR assessment system may be configured to receive an impedance signal of the subject measured during one or more periods after CPR chest compressions by the rescuer and use the impedance signal to establish one or more impedance baselines. The CPR assessment system may be configured to receive an impedance signal of the subject measured during a first period before CPR chest compressions by the rescuer and use the impedance signal to establish a first impedance baseline and receive an impedance signal of the subject measured during one or more subsequent periods after CPR chest compressions by the rescuer and use the impedance signal to establish one or more subsequent impedance baselines.

The CPR assessment system may receive an impedance signal of the subject measured during the plurality of CPR chest compressions by the rescuer over a period of time of approximately 6 seconds, for example. Alternatively, or additionally, the CPR assessment system may receive an impedance signal during a period in which no CPR chest compressions are performed by the rescuer over a period of time of approximately 2 seconds. The CPR assessment system may be configured to assess rate and depth of at least some of the plurality of CPR chest compressions by the rescuer.

An impedance measurement system consistent with the present disclosure may measure the impedance signals of the subject by acquiring signals through electrodes of a defibrillator placed on the chest of the subject or may include a set of electrodes that are independent of a defibrillator.

A bio-signal measurement system may be configured to measure bio-signals of the subject in the form of electrocardiograph (ECG) bio-signals. Such a bio-signal measurement system may apply an algorithm to the ECG bio-signals to determine if the subject is exhibiting a condition which requires a defibrillation shock or a condition which requires CPR. Variations of the exemplary steps discussed above are reviewed:

Steps (v) to (vii) may further include:
(v) when the chest recoil of the subject is greater than the chest recoil threshold, produce the second feedback signal and go to step (vii)(a),
(vi) when the chest recoil of the subject is less than the chest recoil threshold, produce the third feedback signal and go to step (vii)(b),
(vii)(a) when the CPR stop signal is not received, wait for a plurality of CPR chest compressions, return to step (ii),
(vii)(b) when the CPR stop signal is not received, return to step (ii).

Step (ii) may be further include:
(ii)(a) set a CPR counter equal to x,
(ii)(b) receive an impedance signal of the subject measured during a plurality of CPR chest compressions by the rescuer,
(ii)(c) receive a CPR chest compression rate measured during the plurality of CPR chest compressions,
(ii)(d) compare the measured compression rate with a minimum required compression rate,
(ii)(e) when the measured compression rate is greater than the minimum required compression rate, go to step (iii),
(ii)(f) when the measured compression rate is less than the minimum required compression rate, when the CPR counter is not equal to zero, decrease the CPR counter by 1, produce a fifth feedback signal and go to step (ii)(b),
(ii)(g) when the measured compression rate is less than the minimum required compression rate, when the CPR counter is equal to zero, go to step (iii).

Step (ii)(f) may further include when the measured compression rate is less than the minimum required compression rate, when the CPR counter is not equal to zero, decrease the CPR counter by 1, produce a fifth feedback signal, wait for a plurality of compressions and go to step (ii)(b).

Alternatively, step (ii) may further include:
(ii)(a) set a CPR counter equal to x,
(ii)(b) receive an impedance signal of the subject measured during a plurality of CPR chest compressions by the rescuer,
(ii)(c) receive a compression rate measured during the plurality of CPR chest compressions,
(ii)(d) compare the measured compression rate with a maximum required compression rate,
(ii)(e) when the measured compression rate is less than the maximum required compression rate, go to step (iii),
(ii)(f) when the measured compression rate is greater than the maximum required compression rate, when the CPR counter is not equal to zero, decrease the CPR counter by 1, produce a sixth feedback signal and go to step (ii)(b),
(ii)(g) when the measured compression rate is greater than the maximum required compression rate, when the CPR counter is equal to zero, go to step (iii).

Step (ii)(f) may further include when the measured compression rate is greater than the maximum required compression rate, when the CPR counter is not equal to zero, decrease the CPR counter by 1, produce a sixth feedback signal, wait for a plurality of compressions and go to step (ii)(b).

Alternatively, step (ii) may further include:
(ii)(a) set a CPR counter equal to x,
(ii)(b) receive an impedance signal of the subject measured during a plurality of CPR chest compressions by the rescuer,
(ii)(c) receive a compression rate measured during the plurality of CPR chest compressions,
(ii)(d) compare the measured compression rate with a minimum required compression rate and a maximum required compression rate,
(ii)(e) when the measured compression rate is greater than the minimum required compression rate and when the measured compression rate is less than the maximum required compression rate, go to step (iii),
(ii)(f) when the measured compression rate is less than the minimum required compression rate, when the CPR counter is not equal to zero, decrease the CPR counter by 1, produce a fifth feedback signal and go to step (ii)(b),
(ii)(g) when the measured compression rate is less than the minimum required compression rate, when the CPR counter is equal to zero, go to step (iii), (ii)(h) when the measured compression rate is greater than the maximum required compression rate, when the CPR counter is not equal to zero, decrease the CPR counter by 1, produce a sixth feedback signal and go to step (ii)(b),
(ii)(i) when the measured compression rate is greater than the maximum required compression rate, when the CPR counter is equal to zero, go to step (iii).

Step (ii)(f) may further include when the measured compression rate is less than the minimum required compression rate, when the CPR counter is not equal to zero, decrease the CPR counter by 1, produce a fifth feedback signal, wait for a plurality of compressions and go to step (ii)(b).

Step (ii)(h) may include when the measured compression rate is greater than the maximum required compression rate, when the CPR counter is not equal to zero, decrease the CPR counter by 1, produce a sixth feedback signal, wait for a plurality of compressions and go to step (ii)(b).

Step (ii) may further include:
(ii)(a) set a CPR counter equal to x,
(ii)(b) receive an impedance signal of the subject measured during a plurality of CPR chest compressions by the rescuer,
(ii)(c) receive a CPR chest compression depth measured during the plurality of CPR chest compressions,
(ii)(d) compare the measured compression depth with a minimum required compression depth, (ii)(e) when the measured compression depth is greater than the minimum required compression depth, go to step (iii), (ii)(f) when the measured compression depth is less than the minimum required compression depth, when the CPR counter is not equal to zero, decrease the CPR counter by 1, produce a seventh feedback signal and go to step (ii)(b), (ii)(g) when the measured compression rate is less than the minimum required compression rate, when the CPR counter is equal to zero, go to step (iii).

Step (ii)(f) may further include when the measured compression depth is less than the minimum required compression depth, when the CPR counter is not equal to zero, decrease the CPR counter by 1, produce a seventh feedback signal, wait for a plurality of compressions and go to step (ii)(b).

Alternatively, step (ii) may further include:

(ii)(a) set a CPR counter equal to x, (ii)(b) receive an impedance signal of the subject measured during a plurality of CPR chest compressions by the rescuer, (ii)(c) receive a compression depth measured during the plurality of CPR chest compressions, (ii)(d) compare the measured compression depth with a maximum required compression depth, (ii)(e) when the measured compression depth is less than the maximum required compression depth, go to step (iii), (ii)(f) when the measured compression depth is greater than the maximum required compression depth, when the CPR counter is not equal to zero, decrease the CPR counter by 1, produce an eighth feedback signal and go to step (ii)(b), (ii)(g) when the measured compression depth is greater than the maximum required compression depth when the CPR counter is equal to zero, go to step (iii).

Step (ii)(f) may further include when the measured compression depth is greater than the maximum required compression depth, when the CPR counter is not equal to zero, decrease the CPR counter by 1, produce an eighth feedback signal, wait for a plurality of compressions and go to step (ii)(b).

Alternatively, step (ii) may further include:

(ii)(a) set a CPR counter equal to x, (ii)(b) receive an impedance signal of the subject measured during a plurality of CPR chest compressions by the rescuer, (ii)(c) receive a compression depth measured during the plurality of CPR chest compressions, (ii)(d) compare the measured compression depth with a minimum required compression depth and a maximum required compression depth, (ii)(e) when the measured compression depth is greater than the minimum required compression depth and when the measured compression depth is less than the maximum required compression depth, go to step (iii), (ii)(f) when the measured compression depth is less than the minimum required compression depth, when the CPR counter is not equal to zero, decrease the CPR counter by 1, produce a seventh feedback signal and go to step (ii)(b), (ii)(g) when the measured compression depth is less than the minimum required compression depth, when the CPR counter is equal to zero, go to step (iii), (ii)(h) when the measured compression depth is greater than the maximum required compression depth, when the CPR counter is not equal to zero, decrease the CPR counter by 1, produce an eighth feedback signal and go to step (ii)(b), (ii)(i) when the measured compression depth is greater than the maximum required compression depth, when the CPR counter is equal to zero, go to step (iii).

Step (ii)(f) may further include when the measured compression depth is less than the minimum required compression depth, when the CPR counter is not equal to zero, decrease the CPR counter by 1, produce a seventh feedback signal, wait for a plurality of compressions and go to step (ii)(b).

Step (ii)(h) may further include when the measured compression depth is greater than the maximum required compression depth, when the CPR counter is not equal to zero, decrease the CPR counter by 1, produce an eighth feedback signal, wait for a plurality of compressions and go to step (ii)(b).

As discussed above, a feedback unit may receive the first feedback signal and issue CPR feedback in the form of a 'Start CPR and Push Hard' instruction to the rescuer or may provide other indications or messages to a rescuer. The feedback unit may receive the second feedback signal and issue CPR feedback in the form of a 'Chest Recoil Incomplete' instruction to the rescuer. The feedback unit may receive the third feedback signal and issue CPR feedback in the form of a 'Chest Recoil Good' instruction to the rescuer. The feedback unit may receive the fourth feedback signal and issue CPR feedback in the form of a 'Stop CPR' instruction to the rescuer. The feedback unit may receive the fifth feedback signal and issue CPR feedback in the form of a 'Push Faster' instruction to the rescuer. The feedback unit may receive the sixth feedback signal and issue CPR feedback in the form of a 'Push Slower' instruction to the rescuer. The feedback unit may receive the seventh feedback signal and issue CPR feedback in the form of a 'Push Harder' instruction to the rescuer. The feedback unit may receive the eighth feedback signal and issue CPR feedback in the form of a 'Push Softer' instruction to the rescuer.

Figure 2:
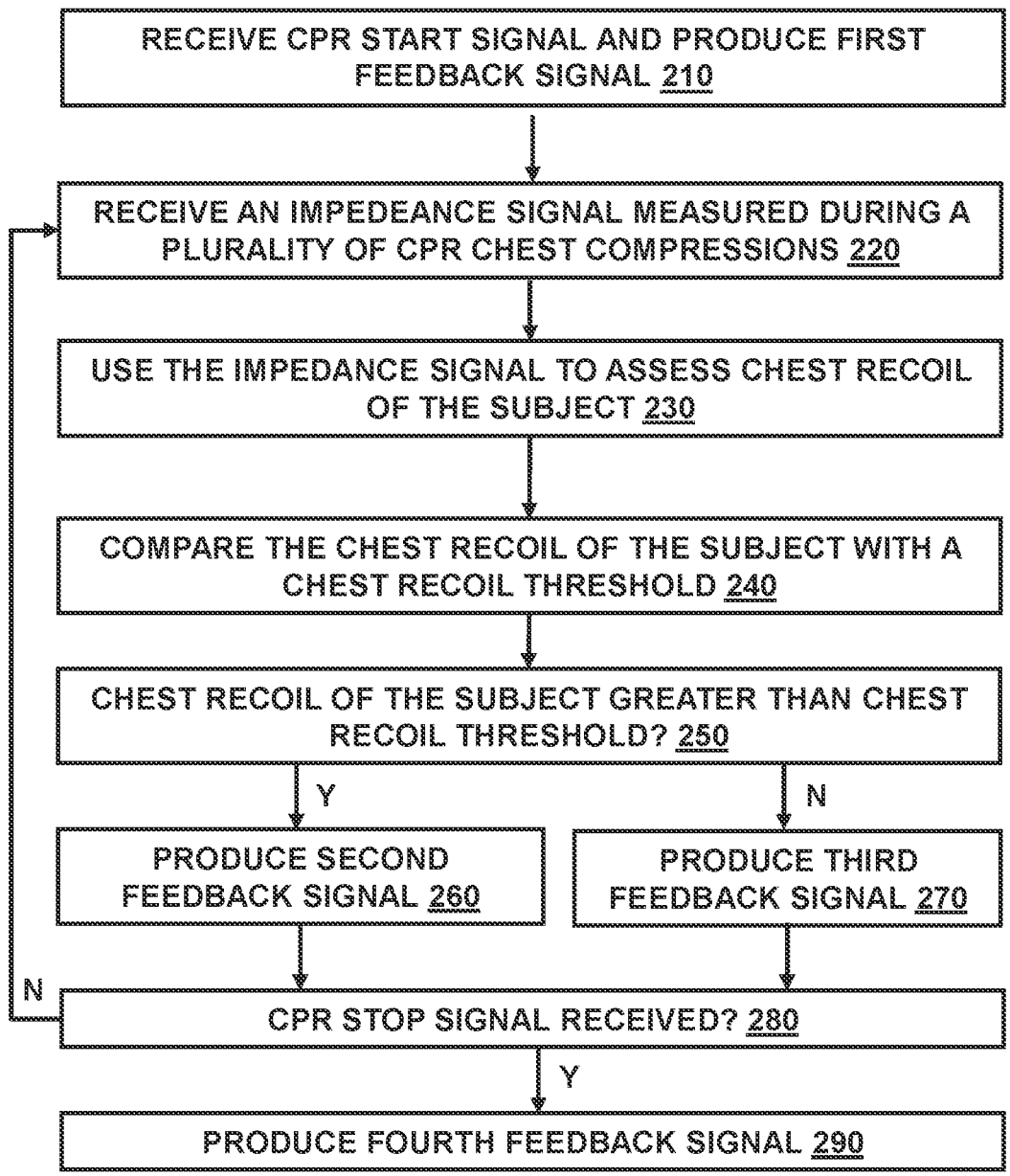
FIG. 2 is a flowchart of steps that may be performed by a CPR assessment system of the defibrillator of FIG. 1.

An embodiment of the disclosure will now be described, by way of example only, with reference to the following drawings, in which FIG. 1 is a schematic representation of a defibrillator or CPR sensing unit consistent with the present disclosure. FIG. 2 is a flowchart of steps that may be performed by a CPR assessment system of the defibrillator of FIG. 1. Referring to FIG. 1, the defibrillator 20 includes a bio-signal measurement system 22, an impedance measurement system 24, a CPR assessment system 26 and a feedback unit 28. The defibrillator 20 assesses CPR carried out by a rescuer (not shown) on a subject (not shown) to assess chest recoil of the subject and provides CPR feedback to the rescuer. As mentioned above, an apparatus consistent with the present disclosure may perform operations of monitoring the efficiency of CPR and may be used to monitor patient bio-signals in a unit that does not include a defibrillator. In such instances, a monitoring/instruction apparatus may be used in conjunction with a defibrillator or coupled to a defibrillator. The bio-signals may be received from a bio-sensor that is capable of sensing heartbeat signals or electrocardiogram (ECG/EKG) signals of a person. The bio-signals may be provided to a controller that controls shocks administered by a defibrillator.

It will be appreciated that the defibrillator 20 can include other elements such as an activation mechanism, a bio-signal processing system, defibrillation shock generation circuitry, a power source and a sensing unit which is adapted to be attached to the subject. Individuals or ordinary skill in the art would understand that a defibrillator is used to shock a patient in order to stimulate the heart of the patient to begin beating again after it has stopped beating.

The bio-signal measurement system 22 may be configured to measure bio-signals of the subject, which, in this embodiment, can include ECG bio-signals. In such instances, a processor or electronic controller may execute instructions to implement an algorithm or analysis based on received ECG bio-signals. Such an analysis may determine whether a subject/patient is exhibiting a condition which requires a defibrillation shock or a condition which requires CPR. When CPR is required, the bio-signal measurement system 22 is configured to produce a CPR start signal. This CPR start signal may generate or provide a message or indicator to a rescuer. When CPR is to stop, the bio-signal measurement system 22 is configured to produce a CPR stop signal.

The impedance measurement system 24 measures the impedance signals of the subject by acquiring signals through electrodes of the defibrillator placed on the chest of the subject. This impedance may be measured by any means known in the art and may include exemplary methods or circuits described later in this document.

The CPR assessment system 26 may be connected to the bio-signal measurement system 22 to receive the CPR start signal and the CPR stop signal. On receipt of the CPR start signal, the CPR assessment system 26 receives impedance signals and commences assessment of chest recoil of the subject over multiple CPR chest compressions by the rescuer. This includes performance of a number of steps, described below with reference to FIG. 2, for example. On receipt of the CPR stop signal, the CPR assessment system 26 ceases assessment of chest recoil of the subject. A CPR stop signal may be generated based on a number of chest compressions, may be generated based on an identification that the patient's heart is beating properly, or may be generated after each of these events. In instances when CPR is stopped, instructions to resume CPR or to provide a defibrillator shock to the patient may be provided to the rescuer.

The CPR assessment system 26 may be connected to the impedance measurement system 24 and receives impedance signals indicative of CPR chest compressions comprising transthoracic impedance signals and uses these to assess chest recoil of the subject over multiple pluralities of CPR chest compressions carried out by the rescuer on the subject. During assessment of the chest recoil of the subject, the CPR assessment system 26 produces various feedback signals. The feedback unit 28 is connected to the CPR assessment system 26 and is configured to receive the feedback signals and issue CPR feedback to the person.

FIG. 2 is a flowchart of steps that may be performed by a CPR assessment system of the defibrillator of FIG. 1. Referring to FIG. 2, the steps performed by the CPR assessment system 26 of the defibrillator 20 of FIG. 1 will be described.

On receipt of the CPR start signal in step 210 of FIG. 2, the CPR assessment system 26 produces a first feedback signal. The first feedback signal is received by the feedback unit 28, which issues CPR feedback in the form of a 'Start CPR and Push Hard' instruction, to the rescuer carrying out CPR on the subject.

The CPR assessment system 26 of FIG. 1 may then receive an impedance signal of the subject in step 220. This impedance may be measured during a plurality of CPR chest compressions by the rescuer over a period of time of approximately 6 seconds, for example. This impedance signal or impedance data may be used to assess chest recoil of the subject during the plurality of CPR chest compressions. The CPR assessment system 26 uses the impedance signal to assess chest recoil by measuring a characteristic of the impedance signal in step 230 of FIG. 2. This may include identifying an amplitude, after at least some, preferably each, of the plurality of CPR chest compressions.

The CPR assessment system 26 then compares the amplitude of the impedance signal in step 240 of FIG. 2. The comparison may be performed after at least some, preferably each, of the plurality of CPR chest compressions with an impedance baseline of the subject. The impedance signal of the subject may include a series of peaks and troughs corresponding to the plurality of CPR chest compressions by the rescuer and the CPR assessment system 26 may compare the amplitude of a trough or a peak of the impedance signal after at least some, preferably each, of the plurality of CPR chest compressions with the impedance baseline of the subject.

The CPR assessment system 26 then may identify whether the chest compressions or a proportion of chest compressions correspond to an incomplete chest recoil or a complete chest recoil in step 250 of FIG. 2. The identification may be based on identifying an amplitude of the impedance signal. An incomplete recoil may be identified based on a CPR chest compression impedance or impedance changes not meeting or exceeding an impedance baseline. A complete chest recoil may be identified based on an amplitude of the impedance signal after a CPR chest compression being equal to or exceeding the impedance baseline. It will be appreciated that the CPR assessment system 26 may identify a incomplete chest recoil when the amplitude of or a change in the impedance signal after a CPR chest compression is not is not within a predetermined tolerance of the impedance baseline. A complete chest recoil can also be identified when the amplitude of the impedance signal after a CPR chest compression is not within a predetermined tolerance of the impedance baseline. The predetermined tolerance may be approximately 10% of the amplitude of the impedance signal after a CPR chest compression.

The CPR assessment system 26 may identify a proportion of incomplete chest recoils and compare the chest recoil of the subject with a chest recoil threshold by comparing the proportion of incomplete chest recoils with the chest recoil threshold, which may be a proportion of incomplete chest recoils of 25%. The CPR assessment system 26 may produce a second feedback signal when the proportion of incomplete chest recoils is greater than the chest recoil threshold in step 270. This indication may be received by the feedback unit 28, which issues CPR feedback, in the form of a 'Chest Recoil Incomplete' instruction, to the rescuer carrying out CPR on the subject. Alternatively, the CPR assessment system 26 produces a third feedback signal when the proportion of incomplete chest recoils is less than or equal to the chest recoil threshold in step 260. These signals may be received by the feedback unit 28, which may then issue CPR feedback in the form of a 'Chest Recoil Good' instruction to the rescuer carrying out CPR on the subject.

The CPR assessment system 26 then checks for receipt of the CPR stop signal from the bio-signal measurement system 22 in step 280 of FIG. 2. As discussed above this determination may be based on a set of criteria. When the CPR stop signal has not been received, the CPR assessment system 26 returns to step 220 of FIG. 2, where an impedance signal is received during a plurality of CPR chest compressions by the rescuer. When the CPR stop signal is received in step 280, the CPR assessment system 26 produces a fourth feedback signal in step 290. The feedback unit 28 receives the fourth feedback signal and issues CPR feedback in the form of a 'Stop CPR' instruction to the rescuer carrying out CPR on the subject. The stop CPR message may be provided based on various criteria as discussed above. This criterion may also require that a percentage or proportion of complete CPR at least meet a threshold level before stop CPR message is issued. To determine the impedance baseline of the subject, the impedance measurement system 24 is configured to measure impedance signals during at least one period in which no CPR chest compressions are performed by the rescuer. The CPR assessment system 26 is configured to receive an impedance signal of the subject measured during the at least one period in which no CPR chest compressions are performed by the rescuer and use the impedance signal to establish the impedance baseline of the subject. In a preferred embodiment, the CPR assessment system 26 is configured to receive an impedance signal of the subject measured during a first period before CPR chest compressions by the rescuer and to use the impedance signal to establish a first impedance baseline. The CPR assessment system 26 can receive an impedance signal of the subject measured during one or more subsequent periods after CPR chest compressions by the rescuer and use the impedance signal to establish one or more subsequent impedance baselines.

Each subsequent impedance baseline may replace a previous impedance baseline. The first period is when the defibrillator 20 is making a decision as to whether the subject is exhibiting a condition which requires a defibrillation shock or a condition which requires CPR. The one or more subsequent periods are when the defibrillator 20 instructs the rescuer to cease CPR chest compressions.

The CPR assessment system 26 receives an impedance signal of the subject measured during the period in which no CPR chest compressions are performed by the rescuer and uses an amplitude of the impedance signal to establish the impedance baseline of the subject. When the subject is experiencing a condition which requires a defibrillation shock, i.e. ventricular fibrillation or ventricular tachycardia, the impedance signal of the subject measured during the period in which no CPR chest compressions are performed by the rescuer is a substantially flat line. The aim of the systems and methods disclosed herein is to achieve as close to complete chest recoil as possible after each CPR chest compression and the defibrillator provides appropriate feedback to the rescuer to try to achieve this. The exemplary steps performed by the CPR assessment system 26 may further include as follows.

Steps (v) to (vii) may further include:
(v) when the chest recoil of the subject is greater than the chest recoil threshold, produce the second feedback signal and go to step (vii)(a),
(vi) when the chest recoil of the subject is less than the chest recoil threshold, produce the third feedback signal and go to step (vii)(b),
(vii)(a) when the CPR stop signal is not received, wait for a plurality of CPR chest compressions, return to step (ii),
(vii)(b) when the CPR stop signal is not received, return to step (ii).

The CPR assessment system 26 may be configured to assess rate and depth of at least some of a plurality of CPR chest compressions by the rescuer.

Step (ii) may further include:
(ii)(a) set a CPR counter equal to x,
(ii)(b) receive an impedance signal of the subject measured during a plurality of CPR chest compressions by the rescuer,
(ii)(c) receive a CPR chest compression rate measured during the plurality of CPR chest compressions,
(ii)(d) compare the measured compression rate with a minimum required compression rate,
(ii)(e) when the measured compression rate is greater than the minimum required compression rate, go to step (iii),
(ii)(f) when the measured compression rate is less than the minimum required compression rate, when the CPR counter is not equal to zero, decrease the CPR counter by 1, produce a fifth feedback signal and go to step (ii)(b),
(ii)(g) when the measured compression rate is less than the minimum required compression rate, when the CPR counter is equal to zero, go to step (iii).

Step (ii)(f) may further include when the measured compression rate is less than the minimum required compression rate, when the CPR counter is not equal to zero, decrease the CPR counter by 1, produce a fifth feedback signal, wait for a plurality of compressions and go to step (ii)(b).

Alternatively, step (ii) may further include:
(ii)(a) set a CPR counter equal to x,
(ii)(b) receive an impedance signal of the subject measured during a plurality of CPR chest compressions by the rescuer,
(ii)(c) receive a compression rate measured during the plurality of CPR chest compressions,
(ii)(d) compare the measured compression rate with a maximum required compression rate,
(ii)(e) when the measured compression rate is less than the maximum required compression rate, go to step (iii),
(ii)(f) when the measured compression rate is greater than the maximum required compression rate, when the CPR counter is not equal to zero, decrease the CPR counter by 1, produce a sixth feedback signal and go to step (ii)(b),
(ii)(g) when the measured compression rate is greater than the maximum required compression rate, when the CPR counter is equal to zero, go to step (iii).

Step (ii)(f) may further include when the measured compression rate is greater than the maximum required compression rate, when the CPR counter is not equal to zero, decrease the CPR counter by 1, produce a sixth feedback signal, wait for a plurality of compressions and go to step (ii)(b).

Alternatively, step (ii) may further include:
(ii)(a) set a CPR counter equal to x,
(ii)(b) receive an impedance signal of the subject measured during a plurality of CPR chest compressions by the rescuer,
(ii)(c) receive a compression rate measured during the plurality of CPR chest compressions,
(ii)(d) compare the measured compression rate with a minimum required compression rate and a maximum required compression rate,
(ii)(e) when the measured compression rate is greater than the minimum required compression rate and when the measured compression rate is less than the maximum required compression rate, go to step (iii),
(ii)(f) when the measured compression rate is less than the minimum required compression rate, when the CPR counter is not equal to zero, decrease the CPR counter by 1, produce a fifth feedback signal and go to step (ii)(b), (ii)(g) when the measured compression rate is less than the minimum required compression rate, when the CPR counter is equal to zero, go to step (iii), (ii)(h) when the measured compression rate is greater than the maximum required compression rate, when the CPR counter is not equal to zero, decrease the CPR counter by 1, produce a sixth feedback signal and go to step (ii)(b), (ii)(i) when the measured compression rate is greater than the maximum required compression rate, when the CPR counter is equal to zero, go to step (iii).

Step (ii)(f) may further include when the measured compression rate is less than the minimum required compression rate, when the CPR counter is not equal to zero, decrease the CPR counter by 1, produce a fifth feedback signal, wait for a plurality of compressions and go to step (ii)(b).

Step (ii)(h) may further include when the measured compression rate is greater than the maximum required compression rate, when the CPR counter is not equal to zero, decrease the CPR counter by 1, produce a sixth feedback signal, wait for a plurality of compressions and go to step (ii)(b).

Step (ii) may further include:

(ii)(a) set a CPR counter equal to x, (ii)(b) receive an impedance signal of the subject measured during a plurality of CPR chest compressions by the rescuer, (ii)(c) receive a CPR chest compression depth measured during the plurality of CPR chest compressions, (ii)(d) compare the measured compression depth with a minimum required compression depth, (ii)(e) when the measured compression depth is greater than the minimum required compression depth, go to step (iii), (ii)(f) when the measured compression depth is less than the minimum required compression depth, when the CPR counter is not equal to zero, decrease the CPR counter by 1, produce a seventh feedback signal and go to step (ii)(b), (ii)(g) when the measured compression rate is less than the minimum required compression rate, when the CPR counter is equal to zero, go to step (iii).

Step (ii)(f) may further include when the measured compression depth is less than the minimum required compression depth, when the CPR counter is not equal to zero, decrease the CPR counter by 1, produce a seventh feedback signal, wait for a plurality of compressions and go to step (ii)(b).

Alternatively, step (ii) may further include:

(ii)(a) set a CPR counter equal to x, (ii)(b) receive an impedance signal of the subject measured during a plurality of CPR chest compressions by the rescuer, (ii)(c) receive a compression depth measured during the plurality of CPR chest compressions, (ii)(d) compare the measured compression depth with a maximum required compression depth, (ii)(e) when the measured compression depth is less than the maximum required compression depth, go to step (iii), (ii)(f) when the measured compression depth is greater than the maximum required compression depth, when the CPR counter is not equal to zero, decrease the CPR counter by 1, produce an eighth feedback signal and go to step (ii)(b), and (ii)(g) when the measured compression depth is greater than the maximum required compression depth when the CPR counter is equal to zero, go to step (iii).

Step (ii)(f) may further include when the measured compression depth is greater than the maximum required compression depth, when the CPR counter is not equal to zero, decrease the CPR counter by 1, produce an eighth feedback signal, wait for a plurality of compressions and go to step (ii)(b).

Alternatively, step (ii) may further include:

(ii)(a) set a CPR counter equal to x, (ii)(b) receive an impedance signal of the subject measured during a plurality of CPR chest compressions by the rescuer, (ii)(c) receive a compression depth measured during the plurality of CPR chest compressions, (ii)(d) compare the measured compression depth with a minimum required compression depth and a maximum required compression depth, (ii)(e) when the measured compression depth is greater than the minimum required compression depth and when the measured compression depth is less than the maximum required compression depth, go to step (iii), (ii)(f) when the measured compression depth is less than the minimum required compression depth, when the CPR counter is not equal to zero, decrease the CPR counter by 1, produce a seventh feedback signal and go to step (ii)(b), (ii)(g) when the measured compression depth is less than the minimum required compression depth, when the CPR counter is equal to zero, go to step (iii), (ii)(h) when the measured compression depth is greater than the maximum required compression depth, when the CPR counter is not equal to zero, decrease the CPR counter by 1, produce an eighth feedback signal and go to step (ii)(b), (ii)(i) when the measured compression depth is greater than the maximum required compression depth, when the CPR counter is equal to zero, go to step (iii).

Step (ii)(f) may further include when the measured compression depth is less than the minimum required compression depth, when the CPR counter is not equal to zero, decrease the CPR counter by 1, produce a seventh feedback signal, wait for a plurality of compressions and go to step (ii)(b).

Step (ii)(h) may further include when the measured compression depth is greater than the maximum required compression depth, when the CPR counter is not equal to zero, decrease the CPR counter by 1, produce an eighth feedback signal, wait for a plurality of compressions and go to step (ii)(b).

The feedback unit may receive the fifth feedback signal and issue CPR feedback in the form of a 'Push Faster' instruction to the rescuer. The feedback unit may receive the sixth feedback signal and issue CPR feedback in the form of a 'Push Slower' instruction to the rescuer. The feedback unit may receive the seventh feedback signal and issue CPR feedback in the form of a 'Push Harder' instruction to the rescuer. The feedback unit may receive the eighth feedback signal and issue CPR feedback in the form of a 'Push Softer' instruction to the rescuer.

Figure 3:
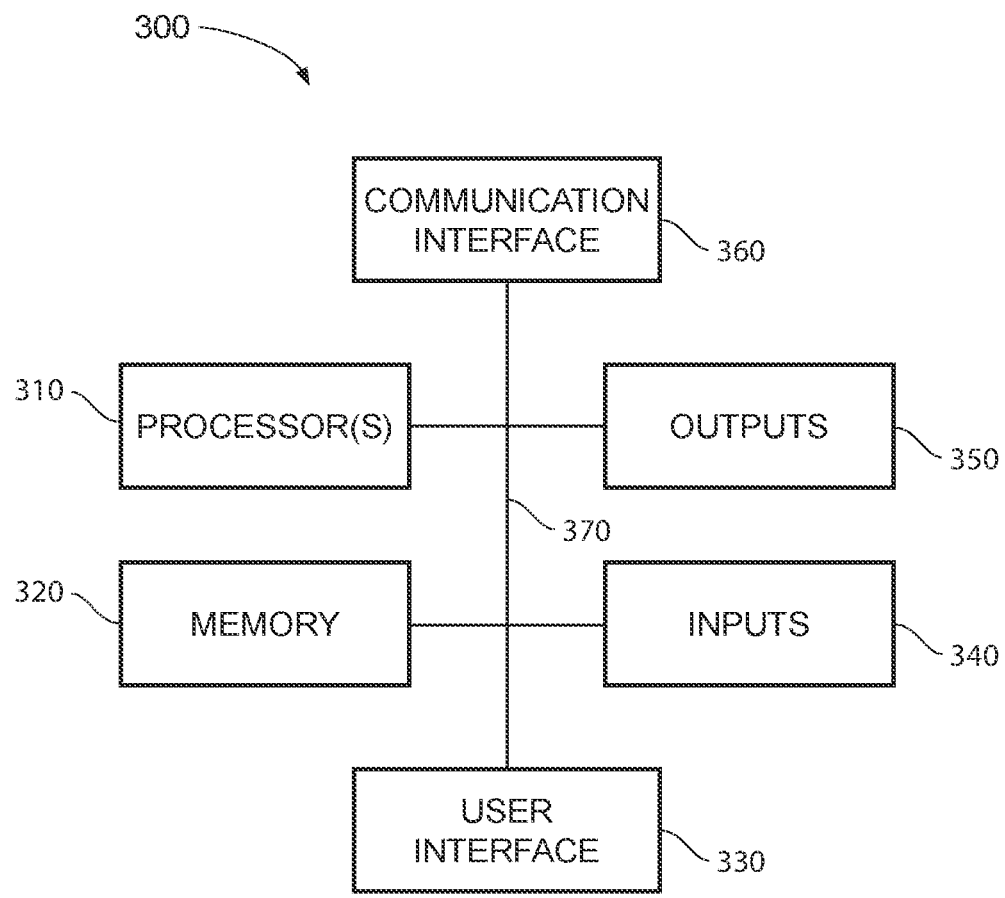
FIG. 3 illustrates electronic components that may be used to control the operation of a CPR assessment apparatus or a defibrillator that includes a CPR assessment unity consistent with the present disclosure.

FIG. 3 illustrates electronic components that may be used to control the operation of a CPR assessment apparatus or a defibrillator that includes a CPR assessment unit consistent with the present disclosure. The Apparatus 300 of FIG. 3 includes one or more processors 310, memory 320, a user interface 330, inputs 330, outputs 350, and a communication interface 360. Various of the different components illustrated in FIG. 3 may be communicatively coupled to each other via a bus 370. In operation, processor(s) 310 may execute instructions out of memory 320 to perform operations of controlling the apparatus 300 as described herein. Processor(s) 310 may be any processor known in the art, yet typically may be a microcontroller executing instructions stored in memory 320. The memory 320 may be any memory known in the art, typically memory 320 will be or include a form of random access memory (RAM). Memory 320 may also include a non-volatile memory (e.g. FLASH memory) that stores firmware program code. In operation, instructions stored in FLASH memory may be moved to RAM as part of an initialization process.

User interface 330 may be any type of user interface known in the art capable of providing indications or messages to users of the apparatus 300. The user interface 330 may be coupled to a display (e.g. a computer display), a speaker, a microphone, or to lights (e.g. LEDS). User interface may provide instructions or information to a user/rescuer as discussed above.

Inputs 340 may be coupled to sensors that sense human biometric data (e.g. bio-sensors) or to collect data such as heart beat/rhythm data (or the lack thereof) or to collect data that may be used to identify an impedance of a patient as CPR is administrated. Inputs 340 may also include or be coupled to an analog-to-digital converter that converts analog sensor data to digital data. In certain instances, inputs 340 may receive digital data directly from a sensor (analog or digital). Outputs 350 may be an energy source that provides a stimulus that may be used to identify an impedance. The energy source may be a voltage source similar to voltage source 310 of FIG. 3 or may be a current source that provides a controlled current. Outputs 350 may include a digital-to-analog converter that provides a stimulus based on binary outputs from a processor.

Stimulus provided to a patient via outputs 350 and data received via inputs 340 may be used to identify an impedance or a change in impedance of a patient as CPR is performed on that patient. In certain instances, outputs 350 may control a defibrillator, where the processor 310 may control when the patient is shocked based on received data and/or based on a rescuer providing input via inputs 340 or the user interface 330 indicating that the patient is "clear." This clear indication may identify that the rescuer is not touching the patient and that the shock may be provided to the patient without shocking the rescuer or another person.

Communication interface 360 may allow the processor 310 to send data to other devices. As such, the communication interface 360 may be or include a computer network interface, a cellular phone interface, or any other computer communication interface known in the art.

While various flow diagrams provided and described above may show a particular order of operations performed by certain embodiments of the disclosure, it should be understood that such order is exemplary (e.g., alternative embodiments can perform the operations in a different order, combine certain operations, overlap certain operations, etc.).

What is claimed is:

1. An apparatus that monitors cardio pulmonary resuscitation (CPR), the apparatus comprising:
   a sensor that senses an impedance signal associated with chest recoil of a person when CPR is administrated to the person;
   a controller that:
   receives the impedance signal sensed by the sensor;
   identifies an amplitude of the impedance signal associated with the chest recoil of the person,
   compares the impedance signal amplitude with impedance baseline data, and
   identifies that a message should be provided to a rescuer based on the comparison of the impedance signal amplitude with the impedance baseline data; and
   a user interface that provides the message to the rescuer.

2. The apparatus of claim 1, further comprising one or more bio-sensors that senses a bio-signal of the person.

3. The apparatus of claim 2, wherein the controller identifies that CPR should be administered to the person based on the received bio-signal.

4. The apparatus of claim 2, further comprising defibrillator electronics configured to provide a shock to the person, wherein the controller identifies that the shock should be provided to the person based on the received bio-signal and the defibrillator electronics provide the shock to the person based on the identification that the shock should be provided to the person.

5. The apparatus of claim 3, wherein:
   the controller identifies that a number of chest compressions has been administered to the person based on the received impedance signal,
   the controller identifies that a stop CPR message should be provided to the and based on the identified number of chest compressions, and
   the stop CPR message is provided to the rescuer via the user interface.

6. The apparatus of claim 1, wherein the user interface includes at least one of a display, a speaker, or an indicator light.

7. The apparatus of claim 1, wherein the controller includes:
   a memory; and
   a processor that executes instructions out of the memory.

8. The apparatus of claim 1, further comprising a communication interface that sends data to and that receives data from an external computing device.

9. A method for evaluating cardio pulmonary resuscitation (CPR),
   receiving an impedance signal associated with chest recoil of a person when CPR is administered to the person;
   identifying an amplitude of the impedance signal associated with the chest recoil of the person;
   comparing the impedance signal amplitude with impedance baseline data;
   identifying that a message should be provided to a rescuer based on the comparison of the impedance signal amplitude with the impedance baseline data; and
   providing the message to the rescuer.

10. The method of claim 9, further comprising identifying that the impedance signal amplitude does not does not meet or exceed a threshold level based on the comparison of the impedance signal amplitude with the impedance baseline data, wherein the message provided to the rescuer indicates that the chest recoil is unacceptable based on the impedance signal amplitude not meeting or exceeding the threshold level.

11. The method of claim 9, further comprising identifying that the impedance signal amplitude meets or exceeds a threshold level based on the comparison of the impedance signal amplitude with the impedance baseline data, wherein the message provided to the rescuer indicates that the chest recoil is acceptable based on the impedance signal amplitude meeting or exceeding the threshold level.

12. The method of claim 9, further comprising calculating a proportion of incomplete chest compressions, wherein the comparison of comparing the impedance signal amplitude with the impedance baseline data includes comparing the proportion of the incomplete chest compressions with a chest recoil threshold.

13. The method of claim 9, further comprising:
receiving a bio-signal of the person;
identifying that CPR should be administered to the person based on the received bio-signal;
identifying that a number of chest compressions has been administered to the person based on the received impedance signal; and
provide a stop CPR message to the rescuer based on the identified number of chest compressions.

14. The method of claim 9, further comprising:
receiving a bio-signal of the person;
identifying that a shock should be administered to the person; and
providing a shock required message to the rescuer, wherein the person is administered the shock after the shock required message is provided to the rescuer.

15. The method of claim 9, wherein the message provided to the rescuer instructs the rescuer to perform an operation that includes at least one of pushing harder, pushing softer, pushing faster, or pushing slower during the administration of CPR to the person.

16. A defibrillator which assesses chest recoil of a subject during cardio pulmonary resuscitation (CPR) carried out by a rescuer on the subject and provides feedback to the rescuer, the defibrillator comprising:
a bio-signal measurement system configured to measure bio-signals of the subject, identify when CPR is required and produce a CPR start signal and identify when CPR is to be ceased and produce a CPR stop signal,
an impedance measurement system configured to measure impedance signals of the subject,
a CPR assessment system connected to the bio-signal measurement system to receive the CPR start signal and the CPR stop signal, wherein the CPR assessments system is also connected to the impedance measurement system to receive impedance signals and configured to perform the steps:
(i) receiving the CPR start signal and produce a first feedback signal,
(ii) receiving an impedance signal of the subject measured during a plurality of CPR chest compressions by the rescuer,
(iii) use the impedance signal to assess chest recoil of the subject during the plurality of CPR chest compressions,
(iv) comparing the chest recoil of the subject with a chest recoil threshold,
(v) when the chest recoil of the subject is greater than the chest recoil threshold, producing a second feedback signal and going to step (vii),
(vi) when the chest recoil of the subject is less than the chest recoil threshold, producing a third feedback signal and going to step (vii),
(vii) when the CPR stop signal is not received, returning to step (ii),
(viii) when the CPR stop signal is received, producing a fourth feedback signal, and
a feedback unit connected to the CPR assessment system configured to receive the feedback signals and to issue CPR feedback information to the rescuer.

17. The defibrillator of claim 16, wherein the CPR assessment system uses the impedance signal to assess chest recoil of the subject during the plurality of CPR chest compressions by measuring a characteristic of the impedance signal after at least some of the plurality of CPR chest compressions.

18. The defibrillator of claim 17, wherein the CPR assessment system uses the impedance signal to assess chest recoil of the subject during the plurality of CPR chest compressions by measuring an amplitude of the impedance signal after at least some of the plurality of CPR chest compressions.

19. The defibrillator of to claim 18, wherein the CPR assessment system compares the amplitude of the impedance signal after at least some of the plurality of CPR chest compressions with an impedance baseline of the subject.

20. The defibrillator of claim 19, wherein the CPR assessment system determines either incomplete chest recoil when the amplitude of the impedance signal after a CPR chest compression is not within a predetermined tolerance of the impedance baseline or complete chest recoil when the amplitude of the impedance signal after a CPR chest compression is within a predetermined tolerance of the impedance baseline.

21. The defibrillator of claim 20, wherein the CPR assessment system determines a proportion of incomplete chest recoils and compares the chest recoil of the subject with the chest recoil threshold by comparing the proportion of incomplete chest recoils with the chest recoil threshold.

22. The defibrillator of claim 21, wherein the CPR assessment system produces the second feedback signal when the proportion of incomplete chest recoils is greater than the chest recoil threshold and produces the third feedback signal when the proportion of incomplete chest recoils is less than the chest recoil threshold.

23. The defibrillator of claim 20, wherein the CPR assessment system is configured to receive an impedance signal of the subject measured during at least one period in which no CPR chest compressions are performed by the rescuer and use the impedance signal to establish the impedance baseline of the subject.

24. The defibrillator of claim 23, wherein the CPR assessment system may be configured to receive an impedance signal of the subject measured during a first period before CPR chest compressions by the rescuer and use the impedance signal to establish a first impedance baseline and receive an impedance signal of the subject measured during one or more subsequent periods after CPR chest compressions by the rescuer and use the impedance signal to establish one or more subsequent impedance baselines.

25. The defibrillator of claim 16, wherein the impedance measurement system measures the impedance signals of the subject by acquiring signals through electrodes of the defibrillator placed on the chest of the subject.

26. The defibrillator of claim 16, wherein steps (v) to (vii) further comprise:
(v) when the chest recoil of the subject is greater than the chest recoil threshold, produce the second feedback signal and go to step (vii)(a),
(vi) when the chest recoil of the subject is less than the chest recoil threshold, produce the third feedback signal and go to step (vii)(b),
(vii)(a) when the CPR stop signal is not received, wait for a plurality of CPR chest compressions, return to step (ii),
(vii)(b) when the CPR stop signal is not received, return to step (ii).

27. The defibrillator of claim 16, wherein step (ii) further comprises:
- (ii)(a) set a CPR counter equal to x,
- (ii)(b) receive an impedance signal of the subject measured during a plurality of CPR chest compressions by the rescuer,
- (ii)(c) receive a compression rate measured during the plurality of CPR chest compressions,
- (ii)(d) compare the measured compression rate with a minimum required compression rate and a maximum required compression rate,
- (ii)(e) when the measured compression rate is greater than the minimum required compression rate and when the measured compression rate is less than the maximum required compression rate, go to step (iii),
- (ii)(f) when the measured compression rate is less than the minimum required compression rate, when the CPR counter is not equal to zero, decrease the CPR counter by 1, produce a fifth feedback signal and go to step (ii)(b),
- (ii)(g) when the measured compression rate is less than the minimum required compression rate, when the CPR counter is equal to zero, go to step (iii),
- (ii)(h) when the measured compression rate is greater than the maximum required compression rate, when the CPR counter is not equal to zero, decrease the CPR counter by 1, produce a sixth feedback signal and go to step (ii)(b),
- (ii)(i) when the measured compression rate is greater than the maximum required compression rate, when the CPR counter is equal to zero, go to step (iii).

28. The defibrillator of claim 16, wherein step (ii) further comprises:
- (ii)(a) set a CPR counter equal to x,
- (ii)(b) receive an impedance signal of the subject measured during a plurality of CPR chest compressions by the rescuer,
- (ii)(c) receive a compression depth measured during the plurality of CPR chest compressions,
- (ii)(d) compare the measured compression depth with a minimum required compression depth and a maximum required compression depth,
- (ii)(e) when the measured compression depth is greater than the minimum required compression depth and when the measured compression depth is less than the maximum required compression depth, go to step (iii),
- (ii)(f) when the measured compression depth is less than the minimum required compression depth, when the CPR counter is not equal to zero, decrease the CPR counter by 1, produce a seventh feedback signal and go to step (ii)(b),
- (ii)(g) when the measured compression depth is less than the minimum required compression depth, when the CPR counter is equal to zero, go to step (iii),
- (ii)(h) when the measured compression depth is greater than the maximum required compression depth, when the CPR counter is not equal to zero, decrease the CPR counter by 1, produce an eighth feedback signal and go to step (ii)(b),
- (ii)(i) when the measured compression depth is greater than the maximum required compression depth, when the CPR counter is equal to zero, go to step (iii).

29. The defibrillator of claim 16, wherein the feedback unit receives the first feedback signal and issues CPR feedback in the form of a 'Start CPR and Push Hard' instruction to the rescuer, receives the second feedback signal and issues CPR feedback in the form of a 'Chest Recoil Incomplete' instruction to the rescuer, receives the third feedback signal and issues CPR feedback in the form of a 'Chest Recoil Good' instruction to the rescuer, receives the fourth feedback signal and issues CPR feedback in the form of a 'Stop CPR' instruction to the rescuer.

30. The defibrillator of claim 27, wherein the feedback unit receives the fifth feedback signal and issues CPR feedback in the form of a 'Push Faster' instruction to the rescuer, receives the sixth feedback signal and issues CPR feedback in the form of a 'Push Slower' instruction to the rescuer, receives the seventh feedback signal and issues CPR feedback in the form of a 'Push Harder' instruction to the rescuer, receives the eighth feedback signal and issues CPR feedback in the form of a 'Push Softer' instruction to the rescuer.

31. The defibrillator according to claim 28, wherein the feedback unit receives the fifth feedback signal and issues CPR feedback in the form of a 'Push Faster' instruction to the rescuer, receives the sixth feedback signal and issues CPR feedback in the form of a 'Push Slower' instruction to the rescuer, receives the seventh feedback signal and issues CPR feedback in the form of a 'Push Harder' instruction to the rescuer, receives the eighth feedback signal and issues CPR feedback in the form of a 'Push Softer' instruction to the rescuer.

* * * * *